United States Patent
Kitamura

(10) Patent No.: US 10,452,957 B2
(45) Date of Patent: Oct. 22, 2019

(54) IMAGE CLASSIFICATION APPARATUS, METHOD, AND PROGRAM

(71) Applicant: FUJIFILM CORPORATION, Tokyo (JP)

(72) Inventor: Yoshiro Kitamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 69 days.

(21) Appl. No.: 15/868,240

(22) Filed: Jan. 11, 2018

(65) Prior Publication Data

US 2018/0247154 A1 Aug. 30, 2018

(30) Foreign Application Priority Data

Feb. 27, 2017 (JP) ................. 2017-034541

(51) Int. Cl.
*G06K 9/00* (2006.01)
*G06K 9/62* (2006.01)
*G06T 7/00* (2017.01)
*G06K 9/46* (2006.01)
(Continued)

(52) U.S. Cl.
CPC ......... *G06K 9/628* (2013.01); *G06K 9/00214* (2013.01); *G06K 9/4604* (2013.01); *G06K 9/4628* (2013.01); *G06K 9/6274* (2013.01); *G06K 9/66* (2013.01); *G06T 7/0012* (2013.01); *A61B 6/5205* (2013.01); *A61B 6/5217* (2013.01); *G06K 2209/051* (2013.01); *G06T 2207/10012* (2013.01); *G06T 2207/10081* (2013.01); *G06T 2207/10088* (2013.01); *G06T 2207/30048* (2013.01); *G06T 2207/30101* (2013.01)

(58) Field of Classification Search
CPC ........ G06K 9/628; G06K 9/4604; G06K 9/66; G06T 7/0012; G06T 2207/10088; G06T 2207/30101; G06T 2207/30048; G06T 2207/10081; A61B 6/5205; A61B 6/5217
See application file for complete search history.

(56) References Cited

U.S. PATENT DOCUMENTS 7,421,415 B2 * 9/2008 Dong .................. G06K 9/6256 706/12
7,426,498 B2 * 9/2008 Naphade ............... G06N 20/00 706/20

(Continued)

FOREIGN PATENT DOCUMENTS

JP 2014-202502 A 10/2014
JP 2016-109630 A 6/2016

*Primary Examiner* — Amir Alavi
(74) *Attorney, Agent, or Firm* — Birch, Stewart, Kolasch & Birch, LLP

(57) ABSTRACT

An extraction unit extracts a target object from a three-dimensional image, and a feature point detection unit detects at least one feature point included in the three-dimensional image. A reference axis setting unit sets a reference axis in the three-dimensional image based on the feature amount, and a two-dimensional image generation unit generates a two-dimensional image by projecting a target object, which is included in the three-dimensional image, in a specific projection direction using the reference axis as a reference. A classification unit classifies each pixel of the target object into a plurality of classes based on the two-dimensional image.

16 Claims, 9 Drawing Sheets

(51) Int. Cl.
*G06K 9/66* (2006.01)
*A61B 6/00* (2006.01)

(56) References Cited

U.S. PATENT DOCUMENTS

| | | | | |
|---|---|---|---|---|
| 7,840,062 | B2* | 11/2010 | Boroczky | G06K 9/3233 |
| | | | | 378/62 |
| 8,035,640 | B2* | 10/2011 | Aoyama | G06K 9/00208 |
| | | | | 345/420 |
| 8,805,007 | B2* | 8/2014 | Zhang | G06T 7/344 |
| | | | | 382/103 |
| 9,405,959 | B2* | 8/2016 | Dubberley | G06K 9/4661 |
| 9,476,730 | B2* | 10/2016 | Samarasekera | G06K 9/00637 |
| 9,633,483 | B1* | 4/2017 | Xu | G06T 17/10 |
| 9,846,946 | B2* | 12/2017 | Fan | G06K 9/00201 |
| 10,049,492 | B2* | 8/2018 | Babahajiani | G06T 17/20 |
| 2012/0316855 | A1* | 12/2012 | Park | G01N 21/9501 |
| | | | | 703/13 |
| 2014/0293009 | A1 | 10/2014 | Nakazato | |
| 2017/0326739 | A1 | 11/2017 | Nakazato et al. | |
| 2018/0247154 | A1* | 8/2018 | Kitamura | G06K 9/4628 |

* cited by examiner

IMAGE CLASSIFICATION APPARATUS, METHOD, AND PROGRAM

CROSS REFERENCE TO RELATED APPLICATIONS

The present application claims priority under 35 U.S.C. § 119 to Japanese Patent Application No. 2017-034541 filed on Feb. 27, 2017. The above application is hereby expressly incorporated by reference, in its entirety, into the present application.

BACKGROUND

Field of the Invention

The present invention relates to an image classification apparatus, method, and program for classifying a three-dimensional image into a plurality of classes.

Description of the Related Art

In recent years, due to advances in medical apparatuses (for example, multi-detector type computed tomography (CT) apparatuses), high-quality three-dimensional images with high resolution are used for image diagnosis. Since the three-dimensional image is configured to include a large number of two-dimensional images, the three-dimensional image has a large amount of information. For this reason, it may take time for a doctor to find and diagnose a desired observation part. Therefore, by recognizing an organ of interest, extracting the organ of interest from a three-dimensional image including the organ of interest using a method, such as a maximum intensity projection (MIP) method or a minimum intensity projection (MinIP) method, and performing MIP display or performing volume rendering (VR) display of the three-dimensional image, the visibility of the entire organ or a lesion is increased, and the efficiency of diagnosis is improved.

On the other hand, in order to extract a structure, such as an organ of interest, from a three-dimensional image, it is necessary to detect the structure in the three-dimensional image. In order to classify pixels of interest in an image into a plurality of classes, a method of deep learning has been proposed. Deep learning is a machine learning method using a multilayer neural network constructed by hierarchically connecting a plurality of processing layers. In particular, a so-called convolutional neural network (CNN) has been proposed as a multilayer neural network for classifying a two-dimensional image into a plurality of classes.

In deep learning, in each layer of the multilayer neural network, arithmetic processing is performed on a plurality of different pieces of calculation result data obtained from the preceding hierarchy with respect to input data, that is, feature amount extraction result data. Then, by performing further arithmetic processing on the feature amount data obtained by the above processing in the subsequent processing layer, it is possible to improve the recognition rate of feature amounts and classify the input data into a plurality of classes.

It is conceivable to apply such a deep learning method to the three-dimensional image in order to classify the three-dimensional image into a plurality of classes. For example, in the case of detecting a structure of interest in a three-dimensional image, deep learning is performed on the neural network with the three-dimensional image being an input so that pixels to be processed in the three-dimensional image are classified into a plurality of classes of a structure of interest and a structure of no interest. By using the deep-learned neural network in this manner, it is possible to accurately classify the target pixels of the input three-dimensional image into a structure of interest and a structure of no interest.

In addition, the feature amount of a spin image is known as the feature amount of a three-dimensional image. A spin image is an image formed by data obtained by setting a plane perpendicular to the normal at a certain point of interest on a three-dimensional image, voting peripheral point coordinates onto a cylindrical surface having the normal as its axis in the normal direction and a direction perpendicular to the normal, and expressing the peripheral point coordinates in a two-dimensional manner. A method of extracting a target object from a three-dimensional image using such a spin image has been proposed. For example, JP2016-109630A and JP2014-202502A disclose a method of extracting a target object by extracting a spin image and holding the spin image as a dictionary and performing recognition using the spin image of the target object.

SUMMARY

Since the number of pixels of the three-dimensional image described above is larger than that of the two-dimensional image, the amount of calculation increases in the case of performing learning or classification using the deep learning method. In addition, a significantly large amount of memory is required at the time of calculation. In addition, as the number of pixels increases, the number of patterns that an image input to the neural network can have is very large. For this reason, in order to construct a neural network for classifying a three-dimensional image into a plurality of classes by deep learning, a huge amount of data is required for learning.

Therefore, it is conceivable to reduce the data amount of an image used for deep learning by changing the dimension of the input image from the three dimension to the two dimension by using the spin image described above. However, in the spin image, the acquired feature amount differs depending on the direction of the normal at the point of interest on the three-dimensional image. For this reason, the reliability of the spin image as a feature amount is low, and as a result, there is a possibility that class classification cannot be accurately performed even if the spin image is applied to deep learning.

The invention has been made in view of the above circumstances, and it is an object of the invention to accurately classify a three-dimensional image into a plurality of classes with a small amount of calculation in the case of classifying the three-dimensional image into a plurality of classes.

An image classification apparatus according to the invention is an image classification apparatus for classifying a three-dimensional image into a plurality of classes. The image classification apparatus comprises: feature point detection unit for detecting at least one feature point included in the three-dimensional image; reference axis setting unit for setting a reference axis in the three-dimensional image based on at least the one feature point; two-dimensional image generation unit for generating a two-dimensional image by projecting a target object, which is included in the three-dimensional image, in a specific projection direction using the reference axis as a reference; and classification unit for classifying each pixel of the target object into the plurality of classes based on the two-dimensional image.

"Classifying a three-dimensional image into a plurality of classes" means classifying each pixel forming a three-dimensional image so as to belong to one of structures included in the three-dimensional image or classifying each pixel forming a three-dimensional image so as to belong to a specific structure and other structures included in the three-dimensional image. For example, in the former case, a three-dimensional image of blood vessels of the heart is classified into either a coronary artery or a coronary vein. In the latter case, the respective pixels forming a three-dimensional image are classified into, for example, a blood vessel and a non-blood vessel.

The image classification apparatus according to the invention may further comprise extraction unit for extracting the target object from the three-dimensional image.

In the image classification apparatus according to the invention, the classification unit may be a neural network in which learning is performed by using teacher data for the two-dimensional image in order to classify the target object into the plurality of classes.

In the image classification apparatus according to the invention, in the neural network, a plurality of processing layers may be hierarchically connected to each other.

In the image classification apparatus according to the invention, in the neural network, learning may be performed by using the two-dimensional image of the entire target object as teacher data, and the two-dimensional image generation unit may generate the two-dimensional image of the entire target object.

In the image classification apparatus according to the invention, in the neural network, learning may be performed for each local region of the target object by using the two-dimensional image as teacher data, and the two-dimensional image generation unit may generate the two-dimensional image for each local region of the target object.

In the image classification apparatus according to the invention, the two-dimensional image may be a spin image.

In the image classification apparatus according to the invention, in a case where the target object is blood vessels of a heart, the feature point detection unit may detect at least one of an aortic valve, a mitral valve, or an apical portion as the feature point, and the classification unit may classify the blood vessels of the heart into a coronary artery and a coronary vein.

In the image classification apparatus according to the invention, in a case where the target object is branch blood vessels from an aorta of a human body, the feature point detection unit may detect at least one of an aortic arch, a branch position from an abdominal aorta to an iliac artery, or a spine as the feature point, and the classification unit may classify the branch blood vessels from the aorta into at least one of a carotid artery, a subclavian artery, a celiac artery, a renal artery, a mesenteric artery, or an iliac artery.

In the image classification apparatus according to the invention, the two-dimensional image generation unit may generate the two-dimensional image by generating a tree structure, in which the target object is continuous, and projecting the generated tree structure in the specific projection direction.

A learning apparatus according to the invention is a learning apparatus for performing learning of a neural network by using teacher data for classifying a three-dimensional image into a plurality of classes. The learning apparatus comprises: feature point detection unit for detecting at least one feature point included in the three-dimensional image serving as the teacher data; reference axis setting unit for setting a reference axis in the three-dimensional image serving as the teacher data based on at least the one feature point; two-dimensional image generation unit for generating a two-dimensional image serving as the teacher data by projecting a target object, which is included in the three-dimensional image serving as the teacher data, in a specific projection direction using the reference axis as a reference; and learning unit for learning the neural network so as to output a result of the classification with the two-dimensional image serving as the teacher data being an input.

In the learning apparatus according to the invention, in the neural network, a plurality of processing layers may be hierarchically connected to each other.

An image classification method according to the invention is an image classification method for classifying a three-dimensional image into a plurality of classes. The image classification method comprises: detecting at least one feature point included in the three-dimensional image; setting a reference axis in the three-dimensional image based on at least the one feature point; generating a two-dimensional image by projecting a target object, which is included in the three-dimensional image, in a specific projection direction using the reference axis as a reference; and classifying each pixel of the target object into the plurality of classes based on the two-dimensional image.

A learning method according to the invention is a learning method for performing learning of a neural network by using teacher data for classifying a three-dimensional image into a plurality of classes. The learning method comprises: at least one feature point included in the three-dimensional image serving as the teacher data; setting a reference axis in the three-dimensional image serving as the teacher data based on at least the one feature point; generating a two-dimensional image serving as the teacher data by projecting a target object, which is included in the three-dimensional image serving as the teacher data, in a specific projection direction using the reference axis as a reference; and learning the neural network so as to output a result of the classification with the two-dimensional image serving as the teacher data being an input.

In addition, a program causing a computer to execute the image classification method according to the present invention may be provided.

In addition, a program causing a computer to execute the learning method according to the present invention may be provided.

Another image classification apparatus according to the invention is an image classification apparatus for classifying a three-dimensional image into a plurality of classes, and comprises a memory for storing a command to be executed by a computer and a processor configured to execute the stored command. The processor executes: feature point detection processing for detecting at least one feature point included in a three-dimensional image; reference axis setting processing for setting a reference axis in the three-dimensional image based on at least the one feature point; two-dimensional image generation processing for generating a two-dimensional image by projecting a target object, which is included in the three-dimensional image, in a specific projection direction using the reference axis as a reference; and classification processing for classifying each pixel of the target object into a plurality of classes based on the two-dimensional image.

Another learning apparatus according to the invention is a learning apparatus for performing learning of a neural network by using teacher data for classifying a three-dimensional image into a plurality of classes, and comprises a memory for storing a command to be executed by a computer and a processor configured to execute the stored command. The processor executes: feature point detection processing for detecting at least one feature point included in the three-dimensional image serving as the teacher data; reference axis setting processing for setting a reference axis in the three-dimensional image serving as the teacher data based on at least the one feature point; two-dimensional image generation processing for generating a two-dimensional image serving as the teacher data by projecting a target object, which is included in the three-dimensional image serving as the teacher data, in a specific projection direction using the reference axis as a reference; and learning processing for learning the neural network so as to output a result of the classification with the two-dimensional image serving as the teacher data being an input.

According to the invention, at least one feature point included in the three-dimensional image is detected, and the reference axis is set in the three-dimensional image based on at least the one feature point. Then, the two-dimensional image is generated by projecting the target object included in the three-dimensional image in the specific projection direction with the reference axis as a reference, and each pixel of the target object is classified into a plurality of classes based on the two-dimensional image. Thus, according to the invention, since the classification is performed based on the two-dimensional image generated from the three-dimensional image, it is possible to reduce the amount of data of an image to be used compared with a case of performing classification based on the three-dimensional image. In addition, since the two-dimensional image is generated by projecting the target object included in the three-dimensional image using the reference axis, which is set based on the feature point, as a reference, it is possible to reduce a fluctuation in the feature amount in the two-dimensional image caused by the difference in the subject in the three-dimensional image. Therefore, according to the invention, it is possible to accurately classify the three-dimensional image into a plurality of classes with a small amount of calculation.

DESCRIPTION OF THE PREFERRED EMBODIMENTS

Figure 1:
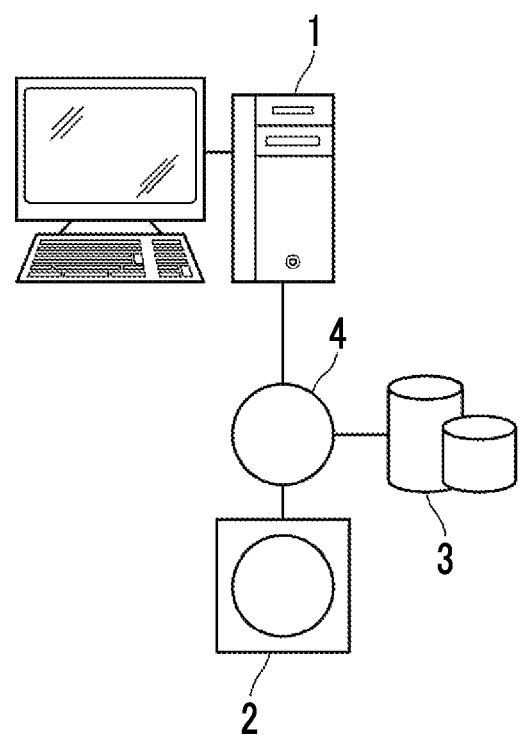
FIG. 1 is a hardware configuration diagram showing the outline of a diagnostic assistance system to which an image classification apparatus and a learning apparatus according to an embodiment of the invention are applied.

Hereinafter, embodiments of the invention will be described with reference to the accompanying diagrams. FIG. 1 is a hardware configuration diagram showing the outline of a diagnostic assistance system to which an image classification apparatus and a learning apparatus according to an embodiment of the invention are applied. As shown in FIG. 1, in this system, an image classification apparatus 1 according to the present embodiment, a three-dimensional image capturing apparatus 2, and an image storage server 3 are communicably connected to each other through a network 4. The learning apparatus according to the present embodiment is included in the image classification apparatus 1.

The three-dimensional image capturing apparatus 2 is an apparatus that generates a three-dimensional image V0 showing a part, which is a surgery target in a subject, by imaging the part. Specifically, the three-dimensional image capturing apparatus 2 is a CT apparatus, a magnetic resonance imaging (MRI) apparatus, a positron emission tomography (PET) apparatus, or the like. The three-dimensional image V0 generated by the three-dimensional image capturing apparatus 2 is transmitted to the image storage server 3 and is stored therein.

The image storage server 3 is a computer that stores and manages various kinds of data, and includes a large-capacity external storage device and software for database management. The image storage server 3 performs communication with other devices through the wired or wireless network 4 to transmit and receive image data or the like. Specifically, the image storage server 3 acquires image data, such as the three-dimensional image V0 generated by the three-dimensional image capturing apparatus 2, through the network, and stores the image data in a recording medium, such as a large-capacity external storage device, and manages the image data. The storage format of image data and the communication between devices through the network 4 is based on a protocol, such as a digital imaging and communication in medicine (DICOM).

The image classification apparatus 1 is realized by installing an image classification program and a learning program of the invention in one computer. The computer may be a workstation or a personal computer that is directly operated by a doctor who performs diagnosis, or may be a server computer connected to these through a network. The image classification program and the learning program are distributed by being recorded on a recording medium, such as a digital versatile disc (DVD) or a compact disk read only memory (CD-ROM), and are installed into the computer from the recording medium. Alternatively, the image classification program and the learning program are stored in a storage device of a server computer connected to the network or in a network storage so as to be accessible from the outside, and are downloaded and installed into a computer used by a doctor as necessary.

Figure 2:
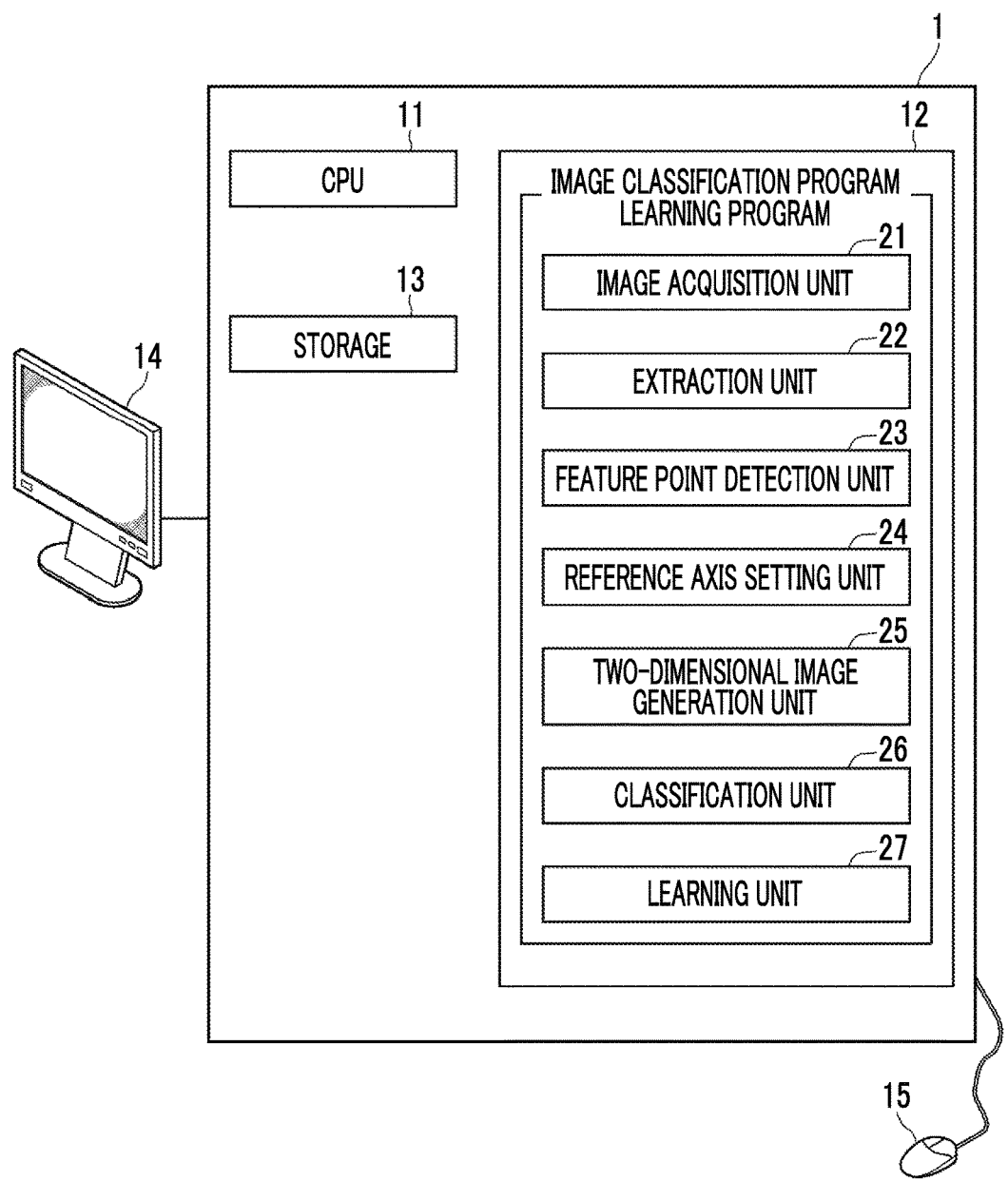
FIG. 2 is a diagram showing the schematic configuration of an image classification apparatus realized by installing an image classification program and a learning program in a computer.

FIG. 2 is a diagram showing the schematic configuration of an image classification apparatus including a learning apparatus, which is realized by installing an image classification program and a learning program in a computer. As shown in FIG. 2, the image classification apparatus 1 includes a central processing unit (CPU) 11 that is a processor, a memory 12, and a storage 13 as the configuration of a standard workstation. A display 14 and an input unit 15, such as a mouse, are connected to the image classification apparatus 1.

Various kinds of information including the three-dimensional image V0, which has been acquired from the image storage server 3 through the network 4, and information necessary for processing in the image classification apparatus 1 to be described later are stored in the storage 13.

An image classification program and a learning program are stored in the memory 12. The memory 12 also serves as a work area in a case where the image classification program and the learning program perform processing. As processing to be executed by the CPU 11, the image classification program defines image acquisition processing for acquiring the three-dimensional image V0 acquired by the three-dimensional image capturing apparatus 2, extraction processing for extracting a target object from the three-dimensional image V0, feature point detection processing for detecting at least one feature point included in the three-dimensional image V0, reference axis setting processing for setting a reference axis in the three-dimensional image V0 based on at least one feature point, two-dimensional image generation processing for generating a two-dimensional image by projecting a target object included in the three-dimensional image V0 in a specific projection direction using the reference axis as a reference, and classification processing for classifying each pixel of the target object into a plurality of classes based on the two-dimensional image. On the other hand, the learning program defines learning processing for learning a neural network, which will be described later, so as to output the classification result with a two-dimensional image serving as teacher data being an input, in addition to the same extraction processing, feature point detection processing, reference axis setting processing, and two-dimensional image generation processing as in the image classification program.

It is assumed that the image classification apparatus 1 of the present embodiment extracts blood vessels of the heart in the three-dimensional image V0 including the heart and classifies the extracted blood vessels into two classes of an artery and a vein, that is, a coronary artery and a coronary vein.

The CPU 11 executes these processes according to the program, so that the computer functions as an image acquisition unit 21, an extraction unit 22, a feature point detection unit 23, a reference axis setting unit 24, a two-dimensional image generation unit 25, a classification unit 26, and a learning unit 27. In the present embodiment, the classification unit 26 is assumed to be a convolutional neural network (CNN) that is one of deep-learned multilayer neural networks in which a plurality of processing layers are hierarchically connected. The image classification apparatus 1 may include a plurality of processors for performing image acquisition processing, extraction processing, feature point detection processing, reference axis setting processing, two-dimensional image generation processing, classification processing, and learning processing.

The image acquisition unit 21 acquires the three-dimensional image V0 from the image storage server 3. In a case where the three-dimensional image V0 is already stored in the storage 13, the image acquisition unit 21 may acquire the three-dimensional image V0 from the storage 13. In the present embodiment, the three-dimensional image V0 is assumed to be a CT image.

The extraction unit 22 extracts a heart from the three-dimensional image V0 first. Specifically, the extraction unit 22 extracts a heart by estimating the range of a signal value (CT value) where the heart is present in the three-dimensional image V0 and performing threshold processing using the value. In addition, the extraction unit 22 extracts blood vessels from the heart as a target object. As a method of extracting blood vessels, for example, a method of calculating a main axis direction and position information of a plurality of candidate points indicating a target tissue having a linear structure and performing reconstruction so that the plurality of candidate points are connected to each other using a cost function that is a variable based on the calculated main axis direction and position information, which is disclosed in JP2010-220742A, or a method of extracting blood vessels so that the blood vessels are automatically distinguished, which is disclosed in JP2011-212314A, can be used.

The feature point detection unit 23 detects at least one feature point included in the three-dimensional image V0. In the present embodiment, three feature points of an aortic valve, a mitral valve, and an apical portion of the heart are detected from the heart extracted from the three-dimensional image V0 by the extraction unit 22. Specifically, blood inlet and outlet in the aortic valve, blood inlet and outlet in the mitral valve, and the most protruding part of the apical portion of the heart are detected as feature points. In a case where the extraction unit 22 does not extract the heart, the feature point detection unit 23 extracts the heart from the three-dimensional image V0 and extracts feature points. Detection of feature points is performed by using a detector generated by learning each of the blood inlet and outlet in the aortic valve, the blood inlet and outlet in the mitral valve, and the most protruding part of the apical portion. Alternatively, templates for the aortic valve, the mitral valve, and the apical portion may be prepared, and feature points may be detected by template matching using the templates.

Figure 3:
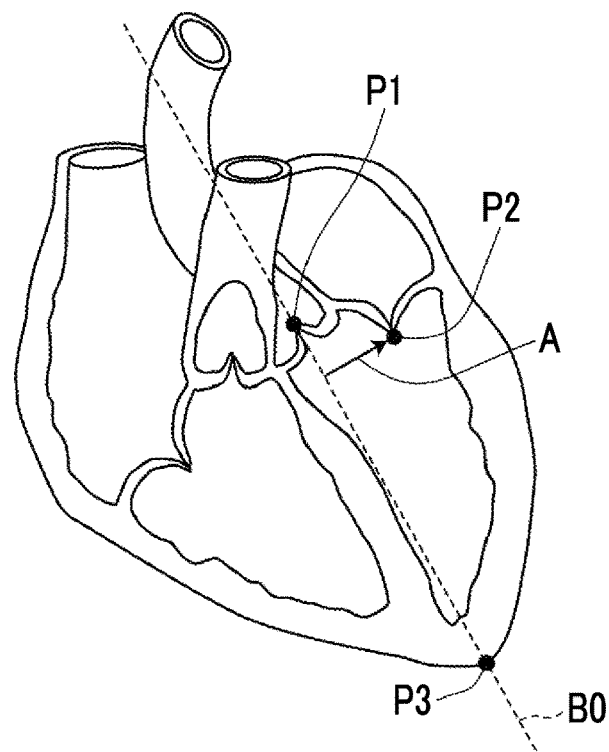
FIG. 3 is a diagram illustrating the setting of a reference axis.

The reference axis setting unit 24 sets a reference axis in the three-dimensional image V0 based on the aortic valve, the mitral valve, and the apical portion detected by the feature point detection unit 23. FIG. 3 is a diagram illustrating the setting of the reference axis. In FIG. 3, an aortic valve P1, a mitral valve P2, and an apical portion P3 in the heart are shown. The reference axis setting unit 24 sets the axis passing through the aortic valve P1 and the apical portion P3 as a reference axis B0. As an angle around the reference axis B0, a direction indicated by the arrow A in which the mitral valve P2 is present is defined as the reference of an angle (that is, 0°). By setting the reference axis B0 in this manner, the posture of the heart can be standardized. In addition, by setting the mitral valve P2 as the reference position of an angle, it is possible to standardize the posture of the heart in the horizontal direction.

The two-dimensional image generation unit 25 generates a two-dimensional image G0 by projecting the target object included in the three-dimensional image V0, that is, the blood vessel of the heart, in a specific projection direction using the reference axis B0 as a reference. In the present embodiment, a spin image is generated as a two-dimensional image. Hereinafter, the spin image will be described.

Figure 4:
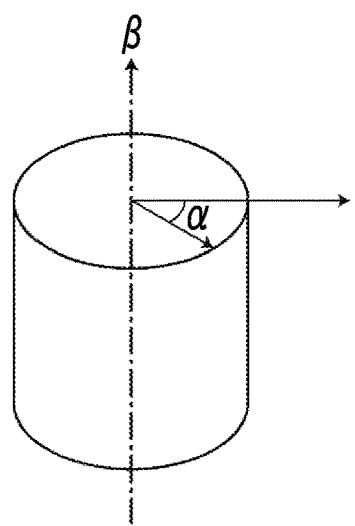
FIG. 4 is a diagram illustrating the generation of a spin image.
Figure 5:
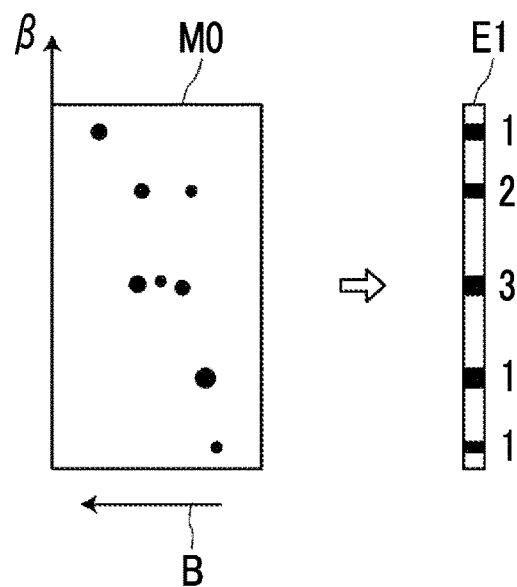
FIG. 5 is a diagram illustrating the generation of a spin image.
Figure 6:
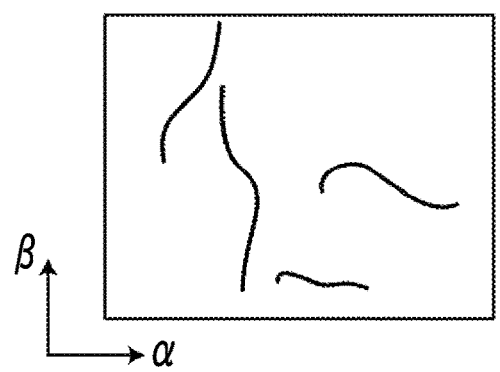
FIG. 6 is a diagram illustrating the generation of a spin image.

FIGS. 4 to 6 are diagrams illustrating the generation of a spin image. The spin image is generated by setting a plane M0 perpendicular to the normal β at a certain point of interest on the image and projecting data on the plane M0 in a direction in which the normal β is present. For example, as shown in FIG. 5, in a case where data is present on the plane M0, projection data E1 configured to include one pixel column extending in the normal direction is obtained by projecting the data of the plane M0 in the direction of arrow B with the normal β. "Projection" in the present embodiment means voting the number of pieces of data present in a pixel column in a direction perpendicular to the normal β. Therefore, as shown in FIG. 5, the number of pieces of data present in a pixel column in the direction perpendicular to the normal β is the pixel value of the projection data E1. For example, the pixel value of the projection data E1 is 3 in a case where three pieces of data are present in a pixel column in the direction perpendicular to the normal β, and the pixel value of the projection data E1 is 0 in a case where there is no data in a pixel column in the direction perpendicular to the normal β.

Alternatively, the spin image may be generated by generating a tree structure by connecting candidate points of blood vessels with the proximity between the candidate points as a reference and projecting a line segment connecting the candidate points to each other. In this manner, in a case where the candidate points are coarsely distributed, it is possible to prevent a path regarded as a blood vessel from appearing discontinuously. As a result, it is possible to generate a spin image in which a blood vessel path is projected more continuously.

Then, the plane perpendicular to the normal β is made to go around the normal, thereby generating a spin image in which the vertical axis is the normal β, the horizontal axis is an angle α around the normal, and each pixel indicates projected data on each plane, as shown in FIG. 6. The spin image is the two-dimensional image G0. In the spin image, a column of pixels on the vertical axis is a projection result of data of the plane perpendicular to the normal β at an angle around the normal corresponding to the column.

In the present embodiment, the reference axis B0 set by the reference axis setting unit 24 is used instead of the normal β, and the two-dimensional image G0 as a spin image is generated by projecting the blood vessel data of the heart extracted by the extraction unit 22 toward the reference axis B0 on each vertical plane while making the plane perpendicular to the reference axis B0 go around the reference axis B0 with the above 0° as a reference. In the present embodiment, one two-dimensional image G0 is generated for all blood vessels of the heart extracted by the extraction unit 22. The two-dimensional image G0 is normalized to a predetermined size.

The classification unit 26 performs classification processing for classifying the blood vessels of the heart into two classes of a coronary artery and a coronary vein based on the two-dimensional image G0, and outputs a classification result. The classification unit 26 is a convolutional neural network as described above. In the convolutional neural network, convolution arithmetic processing is performed on a plurality of different pieces of calculation result data obtained from the preceding hierarchy with respect to input data, that is, feature amount extraction result data, using various kernels in a convolution layer, feature amount data obtained as described above is acquired, and further arithmetic processing is performed on the feature amount data in the subsequent processing layer, so that it is possible to improve the recognition rate of feature amounts and classify the input data into a plurality of classes.

For example, in a convolutional neural network for classifying a two-dimensional image into a plurality of classes, convolution processing using various kernels is performed on an input image in a convolution layer, a feature amount map including feature amount data obtained by the convolution processing is acquired, and further calculation is performed on the acquired feature amount map in the subsequent processing layer, so that it is possible to classify pixels to be processed in the input image into classes.

Figure 7:
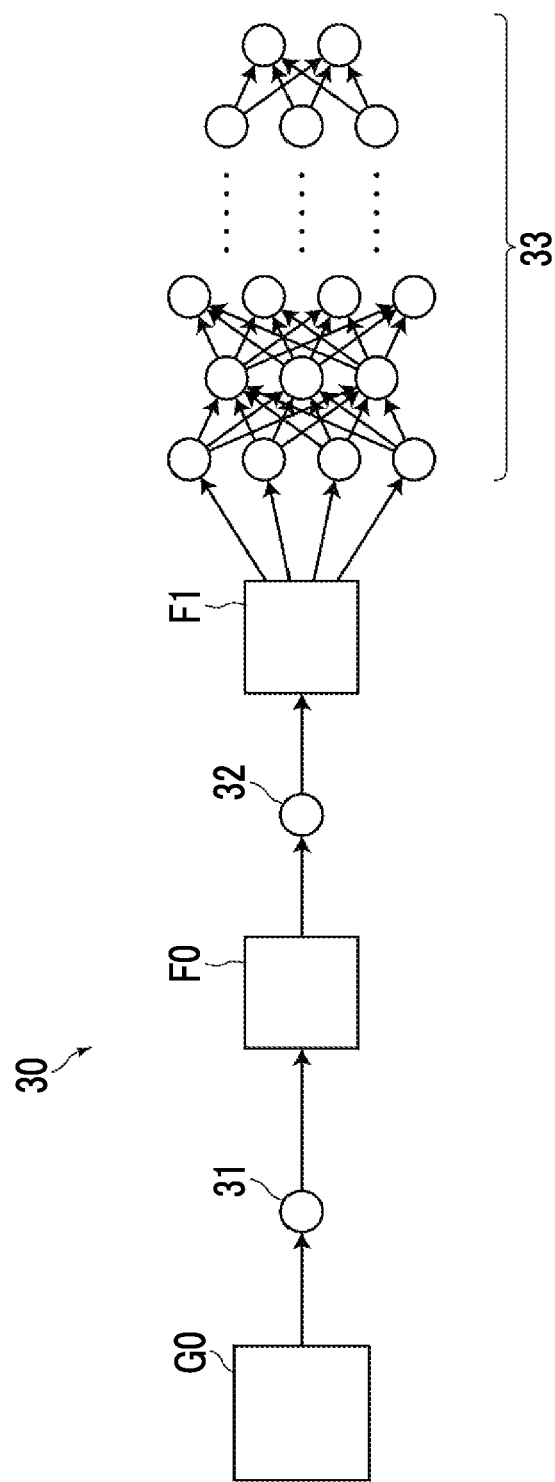
FIG. 7 is a diagram conceptually showing the configuration of a convolutional neural network.

FIG. 7 is a diagram showing an example of the convolution neural network. As shown in FIG. 7, a convolutional neural network (hereinafter, referred to as a CNN) 30 is configured by hierarchically connecting a plurality of processing layers including a convolution layer 31, a pooling layer 32, and an entire coupling layer 33.

The convolution layer 31 performs convolution processing on the two-dimensional image G0 using a predetermined kernel. The kernel has a size of n×n pixels (for example, n=3), and a weight is set for each element. Specifically, a weight, such as a differential filter for emphasizing the edge of the two-dimensional image G0, is set. The convolution layer 31 applies the kernel to the entire two-dimensional image G0 while shifting the pixel of interest of the kernel. The convolution layer 31 applies an activation function, such as a sigmoid function, to the convoluted value, and outputs a feature amount map F0.

The pooling layer 32 reduces the data amount of the feature amount map F0 by pooling the feature amount map F0 output from the convolution layer 31, thereby generating a feature amount map F1.

The entire coupling layer 33 has the same structure as a general multilayer neural network, and is a layer in which all the units among a plurality of processing layers are connected to each other. In FIG. 7, each unit is shown in a circular shape. Coupling between units is indicated by an arrow heading from the input side to the output side. The feature amount map F1 is input to the entire coupling layer 33, and a class classification result as to whether each pixel of the two-dimensional image G0 is a coronary artery or a coronary vein is output.

Here, assuming that inputs and outputs from a plurality of units of the preceding processing layer with respect to a unit of one processing layer in the entire coupling layer 33 are $x_j$ and $y_i$, the weight of coupling between units is $w_{ij}$, and the bias is $b_i$, the output $y_i$ is expressed by the following Equation (1). In Equation (1), f is an activation function, such as a sigmoid function. In Equation (1), the weight $w_{ij}$ and the bias $b_i$ are calculated by learning to be described later.

$$y_i = f(\Sigma_j w_{ij} \bullet x_j + b_j) \quad (1)$$

There are two output layers that are the final hierarchies of the entire coupling layer 33, and one of the two output layers outputs a class classification result indicating whether or not each pixel on the two-dimensional image G0 is a coronary artery. For example, 1 is output in a case where each pixel on the two-dimensional image G0 is a coronary artery, and 0 is output in a case where each pixel on the two-dimensional image G0 is not a coronary artery. The other output layer outputs a class classification result indicating whether or not each pixel on the two-dimensional image G0 is a coronary vein. For example, 1 is output in a case where each pixel on the two-dimensional image G0 is a coronary vein, and 0 is output in a case where each pixel on the two-dimensional image G0 is not a coronary vein. In this manner, the classification unit 26 can classify each pixel on the two-dimensional image G0 into two classes of a coronary artery and a coronary vein. Then, by reflecting the classification result using the two-dimensional image G0 on the three-dimensional image V0 contrary to the case of generating the spin image, it is possible to classify blood vessels of the heart included in the three-dimensional image V0 into coronary arteries and coronary veins.

The learning unit 27 performs learning of the CNN 30. Hereinafter, learning of the CNN 30 will be described. For the learning of the CNN 30, a known error back propagation method is used. A number of teacher data is prepared for the learning of the CNN 30. Teacher data is prepared for each of the coronary artery and the coronary vein. The teacher data of the coronary artery is a spin image that has the same size as the two-dimensional image G0 and is generated only from the coronary artery in the heart. The teacher data of the coronary vein is a spin image that has the same size as the two-dimensional image G0 and is generated only from the coronary vein in the heart.

In the present embodiment, the operator manually extracts the coronary artery and the coronary vein from the heart in the three-dimensional image V0, the feature point detection unit 23 detects three feature points of the aortic valve, the mitral valve, and the apical portion of the heart, the reference axis setting unit 24 sets the axis connecting the aortic valve and the apical portion of the heart to each other as the reference axis B0, and the two-dimensional image generation unit 25 generates spin images of the coronary artery and the coronary vein based on the reference axis B0 as teacher data of two classes.

Figure 8:
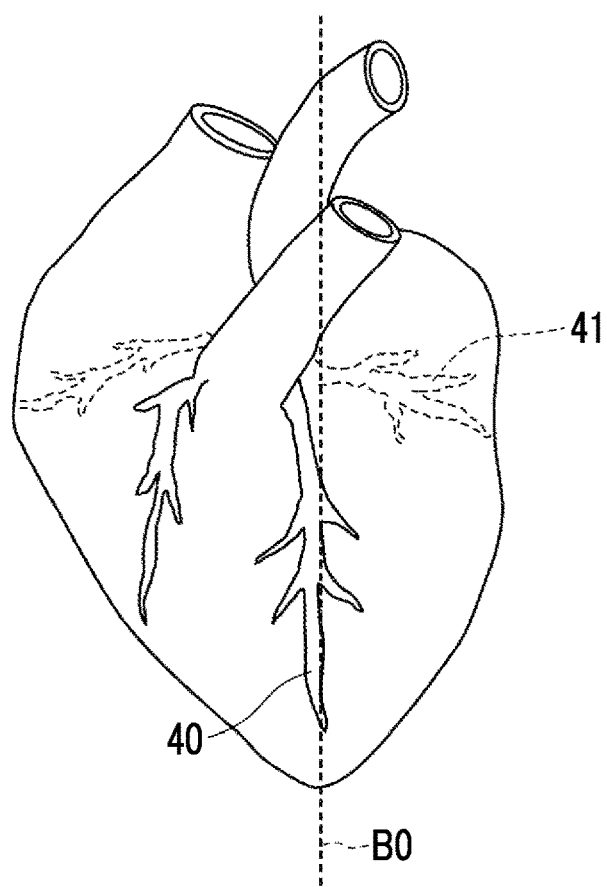
FIG. 8 is a diagram showing blood vessels of the heart.
Figure 9:
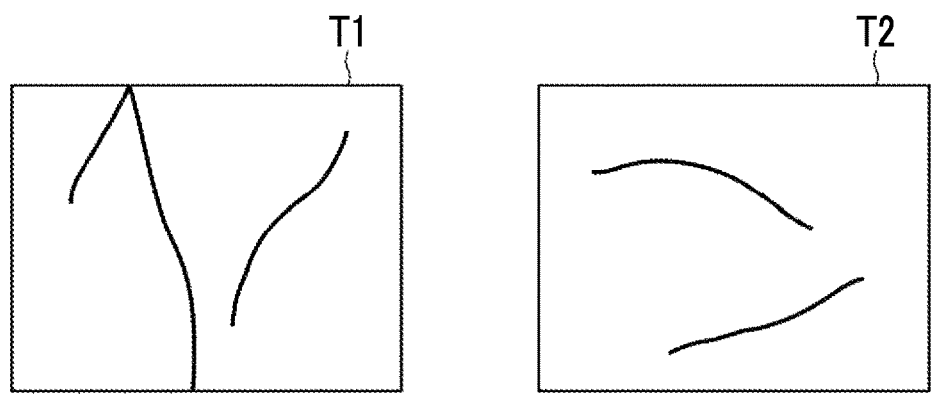
FIG. 9 is a diagram showing an example of teacher data.

FIG. 8 is a diagram showing blood vessels of the heart, and FIG. 9 is a diagram showing an example of teacher data. In FIG. 8, the posture is normalized such that the reference axis B0 connecting the aortic valve and the apical portion to each other is in the vertical direction. As shown in FIG. 8, in a case where the posture is normalized such that the reference axis B0 connecting the aortic valve and the apical portion to each other is in the vertical direction, a coronary artery 40 extends in the vertical direction in the heart, and a coronary vein 41 extends in the horizontal direction in the heart. Therefore, as shown in FIG. 9, teacher data T1 for the coronary artery is data that is continuous in the vertical direction in the two-dimensional image. On the other hand, teacher data T2 for the coronary vein is data that is continuous in the horizontal direction in the two-dimensional image.

Thus, in the spin image, directions in which the coronary artery and the coronary vein extend are different. Therefore, by causing the CNN 30 to learn using the teacher data, it is possible to classify the blood vessels of the heart into coronary arteries and coronary veins.

The learning unit 27 inputs the teacher data to the CNN 30, so that the CNN 30 outputs the class classification result. Then, the learning unit 27 compares the output result with the teacher data, and modifies the bias and the weight of coupling between hierarchies of units included in the entire coupling layer 33, according to whether or not the output classification result is a correct solution or an incorrect solution, from the output side to the input side. The modification of the bias and the weight of coupling is repeated a predetermined number of times or until the accuracy rate of the output classification result becomes 100% using a large number of teacher data, and the learning is ended.

Figure 10:
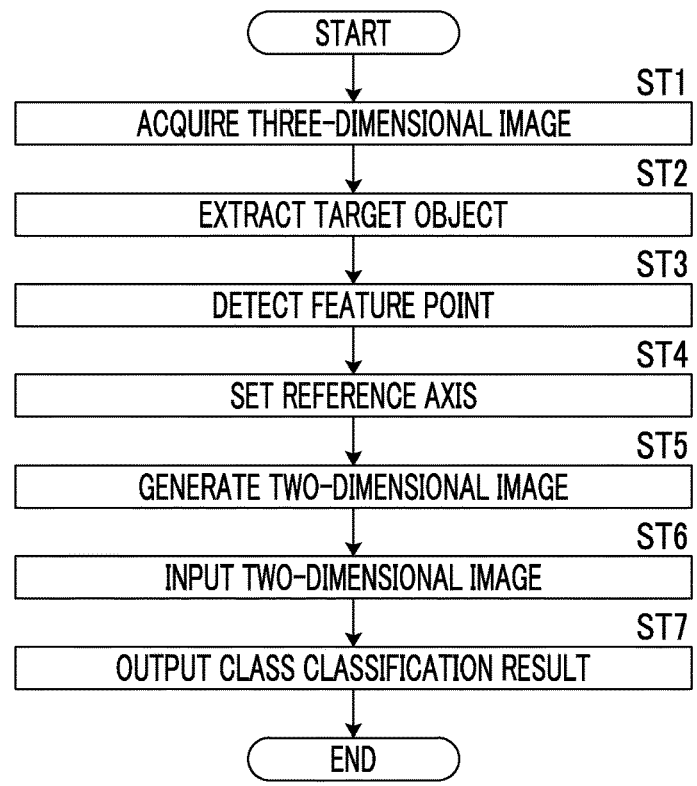
FIG. 10 is a flowchart showing the image classification process performed in the present embodiment.

Next, a process performed in the present embodiment will be described. FIG. 10 is a flowchart showing the image classification process performed in the present embodiment. First, the image acquisition unit 21 acquires the three-dimensional image V0 (step ST1), and the extraction unit 22 extracts a heart and blood vessels of the heart, which are target objects, from the three-dimensional image V0 (step ST2). Then, the feature point detection unit 23 detects an aortic valve, a mitral valve, and an apical portion of the heart, as feature points, from the heart extracted from the three-dimensional image V0 by the extraction unit 22 (step ST3). Then, the reference axis setting unit 24 sets the reference axis B0 in the three-dimensional image V0 based on the aortic valve, the mitral valve, and the apical portion detected by the feature point detection unit 23 (step ST4). Then, the two-dimensional image generation unit 25 generates a spin image of a target object included in the three-dimensional image V0, that is, a spin image of blood vessels, as the two-dimensional image G0 using the reference axis B0 as a reference (step ST5). Then, the classification unit 26 receives an input of the two-dimensional image G0 (step ST6), and outputs the result of the class classification of the blood vessels into coronary arteries and coronary veins (step ST7), and the process is ended.

In addition, it is possible to perform processing, such as deleting coronary veins from the blood vessels extracted from the three-dimensional image V0 based on the class classification result and generating and displaying the tree structure of the coronary arteries by connecting the candidate points of the coronary arteries to each other.

Figure 11:
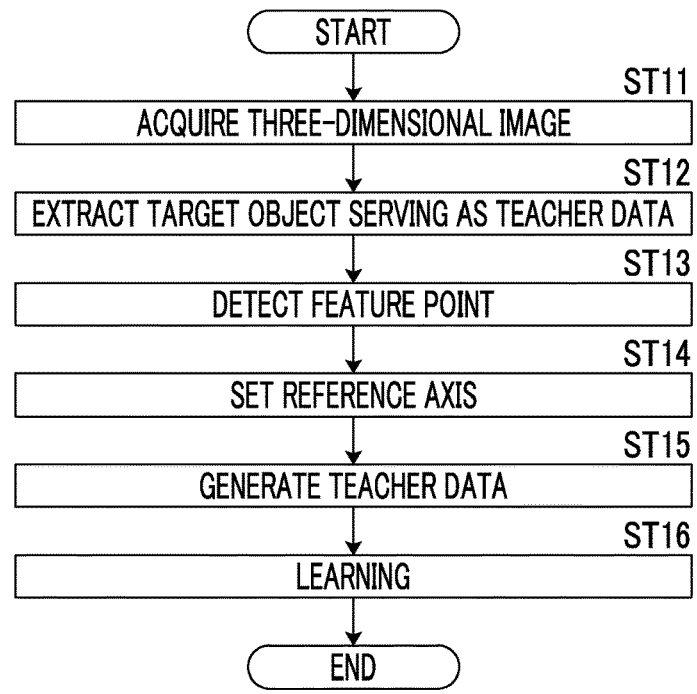
FIG. 11 is a flowchart showing the learning process performed in the present embodiment.

FIG. 11 is a flowchart showing the learning process performed in the present embodiment. It is assumed that the extraction unit 22 extracts the heart from the three-dimensional image V0 for use as teacher data. First, the image acquisition unit 21 acquires the three-dimensional image V0 (step ST11), and the extraction unit 22 extracts the heart from the three-dimensional image V0 and receives an instruction to extract the coronary artery and the coronary vein of the heart, which are target objects to be used as teacher data (step ST12). Specifically, an instruction to manually extract a coronary artery and a coronary vein in the three-dimensional image V0 by the operator is received. Then, the feature point detection unit 23 detects the aortic valve, the mitral valve, and the apical portion of the heart, as feature points, from the heart extracted from the three-dimensional image V0 by the extraction unit 22 (step ST13). Then, the reference axis setting unit 24 sets the reference axis B0 in the three-dimensional image V0 based on the aortic valve, the mitral valve, and the apical portion detected by the feature point detection unit 23 (step ST14). Then, the two-dimensional image generation unit 25 generates a spin image of each of the coronary artery and the coronary vein included in the three-dimensional image V0, as teacher data, using the reference axis B0 as a reference (step ST15). Then, the learning unit 27 learns the CNN 30 of the classification unit 26 so as to output the result of class classification into coronary arteries and coronary veins with a two-dimensional image serving as the teacher data being an input (step ST16), and the process is ended.

As described above, in the present embodiment, at least one feature point included in the three-dimensional image V0 is detected, the reference axis B0 is set in the three-dimensional image V0 based on at least the one feature point, a spin image is generated as the two-dimensional image G0 using the reference axis B0 as a reference, and the blood vessels of the heart are classified into coronary arteries and coronary veins based on the two-dimensional image G0. Thus, according to the present embodiment, since the classification is performed based on the two-dimensional image G0 generated from the three-dimensional image V0, it is possible to reduce the amount of data of an image to be used compared with a case of performing classification based on the three-dimensional image V0. In addition, since the two-dimensional image G0 is generated by projecting a target object included in the three-dimensional image V0 using the reference axis B0, which is set based on the feature points, as a reference, it is possible to reduce a fluctuation in the feature amount in the two-dimensional image G0 caused by the difference in the subject in the three-dimensional image V0. Therefore, according to the present embodiment, it is possible to accurately classify the blood vessels of the heart in the three-dimensional image V0 into two classes of a coronary artery and a coronary vein with a small amount of calculation.

In addition, by making the classification unit 26 serve as the CNN 30 that has performed learning by using the teacher data of the two-dimensional image G0, it is possible to reduce the data amount of the image input to the CNN 30. Therefore, classification using the CNN 30 can be performed with a small amount of calculation.

In addition, by making the CNN 30, in which a plurality of processing layers are hierarchically connected, serve as a neural network, it is possible to perform the more accurate classification by using the feature extraction capability of the CNN 30.

Figure 12:
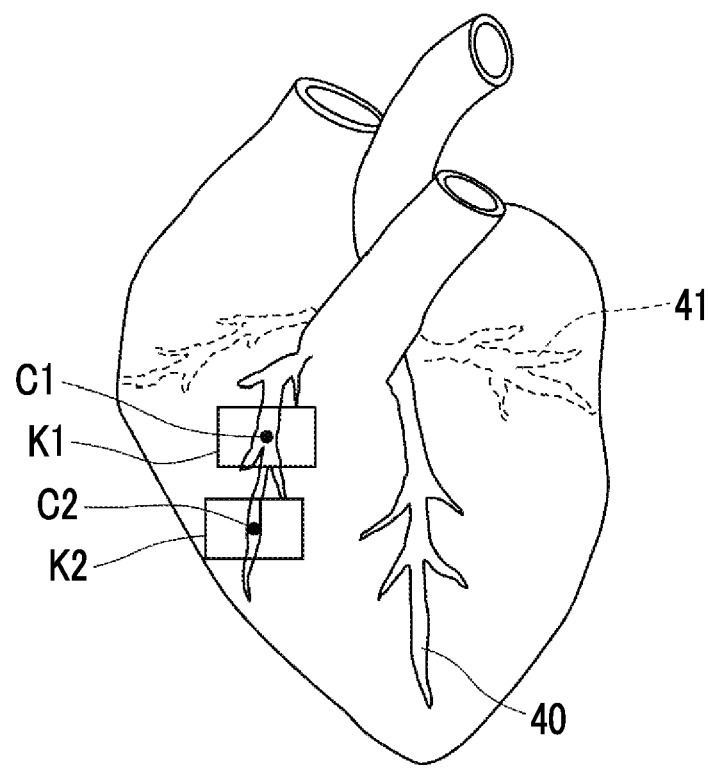
FIG. 12 is a diagram illustrating the generation of a spin image in a local region.

In the embodiment described above, one two-dimensional image G0 is generated for all the blood vessels extracted by the extraction unit 22. However, a plurality of two-dimensional images G0 may be generated for each local region in a blood vessel. For example, in the case of generating a spin image, a plurality of candidate points onto which blood vessel data is projected are set on the heart, and a spin image is generated as the two-dimensional image G0 for each candidate point. For example, as shown in FIG. 12, respective pixels on the heart are set as candidate points C1, C2, . . . , and a spin image is generated as the two-dimensional image G0 for each of regions K1, K2, . . . centered on the candidate point. Then, the two-dimensional image G0 for each region is input to the classification unit 26, and the respective candidate points are classified into two classes of a coronary artery and a coronary vein.

In this case, at the time of learning of the CNN 30 of the classification unit 26, in the coronary artery and the coronary vein at each position on the heart, a spin image is generated from a region having the same size as the regions K1, K2, . . . , and the learning of the CNN 30 is performed using the spin image as teacher data.

In this manner, by generating the two-dimensional image G0 for each candidate point on the heart, it is possible to accurately classify the blood vessels of the heart in the three-dimensional image V0 into two classes of a coronary artery and a coronary vein with a small amount of calculation.

In the embodiment described above, blood vessels of the heart are classified into a coronary artery and a coronary vein. However, as long as other target objects included in the three-dimensional image V0 are classified into a plurality of classes, the invention can be applied to any target object. For example, the invention can also be applied to a case in which, in the three-dimensional image V0 of the entire human body, a target object is branch blood vessels from the aorta, and the blood vessels from the aorta are classified into at least one of the carotid artery, the subclavian artery, the celiac artery, the renal artery, the mesenteric artery, or the iliac artery.

In this case, the extraction unit 22 extracts an artery from the three-dimensional image V0. The feature point detection unit 23 detects at least one of the aortic arch, the branch position from the abdominal aorta to the iliac artery, or the spine in the three-dimensional image as a feature point. In the present embodiment, all of the aortic arch, the branch position from the abdominal aorta to the iliac artery, and the spine are detected as feature points. The reference axis setting unit 24 sets the reference axis B0 using the feature points. Specifically, an axis passing through the aortic arch and the branch position from the abdominal aorta to the iliac artery is set as the reference axis B0. The reference axis B0 and a direction in which the spine is present as viewed from the reference axis B0 are set as reference points (that is, 0°) of the angle around the reference axis B0.

Figure 13:
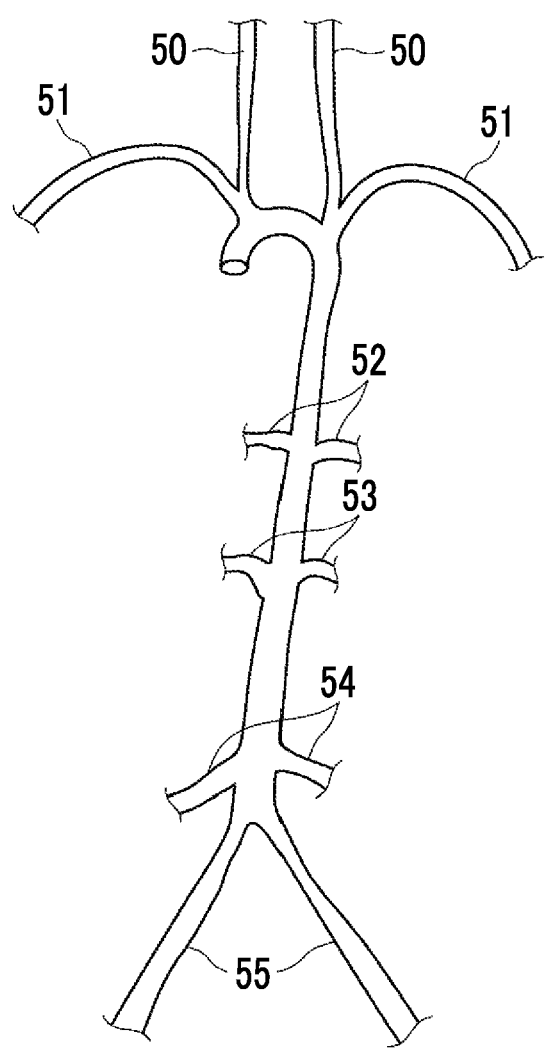
FIG. 13 is a diagram showing the artery of a human body.

Then, similarly to the case of the heart, spin image feature points of branch blood vessels from the aorta with the reference axis B0 as a reference are generated as a two-dimensional image. As shown in FIG. 13, the learning of the CNN 30 is performed so that the classification unit 26 classifies the blood vessels from the aorta into six classes of carotid artery 50, subclavian artery 51, celiac artery 52, renal artery 53, mesenteric artery 54 and iliac artery 55.

By inputting a two-dimensional image to the classification unit 26 in which learning has been performed as described above, the branch blood vessels from the aorta that have been extracted from the three-dimensional image V0 can be classified into the carotid artery, the subclavian artery, the celiac artery, the renal artery, the mesenteric artery, and the iliac artery.

In the embodiment described above, the class classification is performed using the CNN 30 in the classification unit 26. However, the invention is not limited thereto. For example, the class classification may be performed by filtering processing on the two-dimensional image G0 that is a spin image.

In the embodiment described above, a spin image is used as the two-dimensional image G0 for classification. However, the two-dimensional image G0 is not limited to the spin image, and any two-dimensional image G0 can be used as long as the two-dimensional image G0 is generated using the reference axis B0 as a reference. For example, the two-dimensional image G0 may be generated by projecting the three-dimensional image V0 in a predetermined direction using a method, such as volume rendering, with the reference axis B0 as a reference. In this case, the teacher data used for learning may be similarly generated by projecting the three-dimensional image V0 in a predetermined direction using the reference axis B0 as a reference.

In the embodiment described above, the CNN 30 may be constructed so as to classify the three-dimensional image V0 itself into a specific part and other parts. For example, the CNN 30 may be constructed so as to classify the heart included in the three-dimensional image V0 into blood vessels and other parts.

In the embodiment described above, the configuration of the CNN 30 is not limited to that shown in FIG. 7. For example, although one convolution layer 31 and one pooling layer 32 are provided in FIG. 7, a plurality of convolution layers 31 and a plurality of pooling layers 32 may be provided. In this case, in each convolution layer 31, a kernel is set so as to extract different feature amounts from the two-dimensional image G0 and generate a feature point map. In addition, although only one convolution layer 31 is provided, another convolution layer may be further provided at the subsequent stage of the convolution layer 31.

Hereinafter, the effect of the present embodiment will be described.

In order to classify target objects into a plurality of classes, by making classification unit serve as a neural network that has performed learning by using the teacher data of the two-dimensional image, it is possible to reduce the data amount of the image input to the neural network.

Therefore, classification using the neural network can be performed with a small amount of calculation.

In addition, by using the neural network in which a plurality of processing layers are hierarchically connected, it is possible to perform the more accurate classification by using the feature extraction capability of the neural network.

What is claimed is:

1. An image classification apparatus for classifying a three-dimensional image into a plurality of classes, comprising:
processing circuitry configured to:
detect at least one feature point included in the three-dimensional image;
set a reference axis in the three-dimensional image based on at least the one feature point;
generate a two-dimensional image by projecting a target object, which is included in the three-dimensional image, in a specific projection direction using the reference axis as a reference; and
classify each pixel of the target object into the plurality of classes based on the two-dimensional image.

2. The image classification apparatus according to claim 1, wherein the processing circuitry is further configured to extract the target object from the three-dimensional image.

3. The image classification apparatus according to claim 1,
wherein the processing circuitry is further configured to execute a neural network in which learning is performed by using teacher data for the two-dimensional image in order to classify the target object into the plurality of classes.

4. The image classification apparatus according to claim 3,
wherein, in the neural network, a plurality of processing layers are hierarchically connected to each other.

5. The image classification apparatus according to claim 3,
wherein, in the neural network, learning is performed by using the two-dimensional image of the entire target object as teacher data, and
the processing circuitry is further configured to generate the two-dimensional image of the entire target object.

6. The image classification apparatus according to claim 3,
wherein, in the neural network, learning is performed for each local region of the target object by using the two-dimensional image as teacher data, and
the processing circuitry is further configured to generate the two-dimensional image for each local region of the target object.

7. The image classification apparatus according to claim 1,
wherein the two-dimensional image is a spin image.

8. The image classification apparatus according to claim 1,
wherein, in a case where the target object is blood vessels of a heart, the processing circuitry is further configured to detect at least one of an aortic valve, a mitral valve, or an apical portion as the feature point, and
the processing circuitry is further configured to classify the blood vessels of the heart into a coronary artery and a coronary vein.

9. The image classification apparatus according to claim 1,
wherein, in a case where the target object is branch blood vessels from an aorta of a human body, the processing circuitry is further configured to detect at least one of an aortic arch, a branch position from an abdominal aorta to an iliac artery, or a spine as the feature point, and
the processing circuitry is further configured to classify the branch blood vessels from the aorta into at least one of a carotid artery, a subclavian artery, a celiac artery, a renal artery, a mesenteric artery, or an iliac artery.

10. The image classification apparatus according to claim 1,
wherein the processing circuitry is further configured to generate the two-dimensional image by generating a tree structure, in which the target object is continuous, and project the generated tree structure in the specific projection direction.

11. A learning apparatus for performing learning of a neural network by using teacher data for classifying a three-dimensional image into a plurality of classes, comprising:
processing circuitry configured to:
detect at least one feature point included in the three-dimensional image serving as the teacher data;
set a reference axis in the three-dimensional image serving as the teacher data based on at least the one feature point;
generate a two-dimensional image serving as the teacher data by projecting a target object, which is included in the three-dimensional image serving as the teacher data, in a specific projection direction using the reference axis as a reference; and
learn the neural network so as to output a result of the classification with the two-dimensional image serving as the teacher data being an input.

12. The learning apparatus according to claim 11,
wherein, in the neural network, a plurality of processing layers are hierarchically connected to each other.

13. An image classification method for classifying a three-dimensional image into a plurality of classes, comprising:
detecting at least one feature point included in the three-dimensional image;
setting a reference axis in the three-dimensional image based on at least the one feature point;
generating a two-dimensional image by projecting a target object, which is included in the three-dimensional image, in a specific projection direction using the reference axis as a reference; and
classifying each pixel of the target object into the plurality of classes based on the two-dimensional image.

14. A learning method for performing learning of a neural network by using teacher data for classifying a three-dimensional image into a plurality of classes, comprising:
detecting at least one feature point included in the three-dimensional image serving as the teacher data;
setting a reference axis in the three-dimensional image serving as the teacher data based on at least the one feature point;
generating a two-dimensional image serving as the teacher data by projecting a target object, which is included in the three-dimensional image serving as the teacher data, in a specific projection direction using the reference axis as a reference; and
learning the neural network so as to output a result of the classification with the two-dimensional image serving as the teacher data being an input.

15. A non-transitory computer-readable recording medium having stored therein an image classification program causing a computer to execute an image classification method for classifying a three-dimensional image into a plurality of classes, the program causing the computer to execute:
- a step of detecting at least one feature point included in the three-dimensional image;
- a step of setting a reference axis in the three-dimensional image based on at least the one feature point;
- a step of generating a two-dimensional image by projecting a target object, which is included in the three-dimensional image, in a specific projection direction using the reference axis as a reference; and
- a step of classifying each pixel of the target object into the plurality of classes based on the two-dimensional image.

16. A non-transitory computer-readable recording medium having stored therein a learning program causing a computer to execute a learning method for performing learning of a neural network by using teacher data for classifying a three-dimensional image into a plurality of classes, the program causing the computer to execute:
- a step of detecting at least one feature point included in the three-dimensional image serving as the teacher data;
- a step of setting a reference axis in the three-dimensional image serving as the teacher data based on at least the one feature point;
- a step of generating a two-dimensional image serving as the teacher data by projecting a target object, which is included in the three-dimensional image serving as the teacher data, in a specific projection direction using the reference axis as a reference; and
- a step of learning the neural network so as to output a result of the classification with the two-dimensional image serving as the teacher data being an input.

* * * * *